(12) United States Patent
Guo et al.

(10) Patent No.: US 11,771,622 B2
(45) Date of Patent: Oct. 3, 2023

(54) SEALING DEVICE FOR FOOT THERAPEUTIC APPARATUS AND FOOT THERAPEUTIC APPARATUS WITH SEALING DEVICE

(71) Applicant: Jiangsu Medcure Medical Technology Co., Ltd., Qidong (CN)

(72) Inventors: Fang Guo, Shanghai (CN); Junsong Chen, Shanghai (CN); Yi Liu, Shanghai (CN)

(73) Assignee: JIANGSU MEDCURE MEDICAL TECHNOLOGY CO., LTD., Qidong (CN)

( * ) Notice: Subject to any disclaimer, the term of this patent is extended or adjusted under 35 U.S.C. 154(b) by 689 days.

(21) Appl. No.: 16/992,150

(22) Filed: Aug. 13, 2020

(65) Prior Publication Data

US 2021/0393480 A1  Dec. 23, 2021

(30) Foreign Application Priority Data

Jun. 22, 2020 (CN) .......................... 202010570975.3

(51) Int. Cl.
| | | |
|---|---|---|
| *A61H 35/00* | (2006.01) | |
| *A61H 33/00* | (2006.01) | |
| *A61L 31/02* | (2006.01) | |
| *A61L 31/04* | (2006.01) | |

(Continued)

(52) U.S. Cl.
CPC ....... *A61H 35/006* (2013.01); *A61H 33/6005* (2013.01); *A61L 31/022* (2013.01); *A61L 31/049* (2013.01); *G05D 16/2093* (2013.01); *A61H 2033/141* (2013.01); *A61H 2033/143* (2013.01); *A61H 2201/0207* (2013.01); *A61H 2201/1642* (2013.01); *A61H 2201/5071* (2013.01)

(58) Field of Classification Search
CPC .............. A61H 35/006; A61H 33/6005; A61H 2033/141; A61H 2033/143; A61H 2201/0207; A61H 2201/1642; A61H 2201/5071; A61H 33/14; A61L 31/022; A61L 31/049; G05D 16/2093
See application file for complete search history.

(56) References Cited

U.S. PATENT DOCUMENTS

| 5,647,837 A * | 7/1997 | McCarty .................. A61F 5/41 600/38 |
|---|---|---|
| 2008/0045874 A1* | 2/2008 | An ........................ A61M 35/30 602/56 |
| 2021/0059840 A1* | 3/2021 | McGarry .............. A61F 2/5046 |

\* cited by examiner

*Primary Examiner* — Scott M. Getzow
(74) *Attorney, Agent, or Firm* — Bayramoglu Law Offices LLC (57) ABSTRACT

A sealing device for a foot therapeutic apparatus includes an airtight sleeve and a sealing member. The airtight sleeve includes a treatment box connecting end and a limb inlet end. The sealing member is fixedly mounted at the limb inlet end. The sealing member includes a tightening band and an annular gas bag located on the outer periphery of the tightening band. The annular gas bag is connected to a gas source. A foot therapeutic apparatus with the sealing device includes a treatment chamber and an electrical chamber. The treatment chamber comprises a treatment box, and the sealing device is arranged on the treatment box. A box opening is arranged at a top of the treatment box, and the treatment box connecting end of the airtight sleeve of the sealing device is hermetically connected to the box opening.

20 Claims, 9 Drawing Sheets

(51) Int. Cl.
*G05D 16/20* (2006.01)
*A61H 33/14* (2006.01)

SEALING DEVICE FOR FOOT THERAPEUTIC APPARATUS AND FOOT THERAPEUTIC APPARATUS WITH SEALING DEVICE

CROSS REFERENCE TO THE RELATED APPLICATIONS

This application is based upon and claims priority to Chinese Patent Application No. 202010570975.3, filed on Jun. 22, 2020, the entire contents of which are incorporated herein by reference.

TECHNICAL FIELD

The present invention relates to the technical field of foot therapeutic apparatus, and more particularly, to a sealing device for a foot therapeutic apparatus and a foot therapeutic apparatus with the sealing device.

BACKGROUND

A diabetic foot is a serious complication in end-stage diabetes. The World Health Organization defines it as foot infection, foot ulcer and/or destruction of deep tissue caused by diabetic neuropathy and vascular disease of the lower limb. Due to a long-term high blood sugar level, diabetic patients typically have metabolic disorders, which cause angiopathy, especially related to neuropathy, sensory abnormalities and loss of protective function of the foot caused by the serious insufficient blood supply to the foot. Lingering ulcers and infections are prone to diabetic patients and even cause a high risk of amputation. Medical reports have indicated that the diabetic foot is extremely dangerous to the health since amputations caused by the diabetic foot account for more than half of all amputations. In addition to the patient's health disorder(s), the main reasons for the above situation are that the preventive measure to alleviate severe arterial obstruction in the prior art is insufficient; and the treatment method in the prior art for the diabetic foot especially the foot lesion is very limited, and the curative effect is not very satisfactory.

Ozone ($O_3$), also known as super oxygen, is an allotrope of oxygen ($O_2$). At room temperature, ozone is a light blue gas with a special odor. Ozone is mainly distributed in the stratosphere at a height of 10-50 km, and the maximum concentration thereof is distributed at a height of 20-30 km. Under room temperature and standard atmospheric pressure, it has poor stability and will be slowly decomposed into oxygen by itself. The taste of ozone is similar to the taste of grass. A small amount of ozone inhaled is beneficial to the human body, while excessive inhalation is harmful to the human body. Ozone is a non-flammable pure substance. Artificial ozone is prepared usually by electrolysis or irradiation of ultraviolet radiation.

Ozone has broad application in the medical field since it can effectively sterilize and disinfect bacteria. Ozone is a kind of strong oxidant, having an extremely unstable molecular structure, and it can decompose to produce monoatomic oxygen (O) and hydroxyl (OH), with strong oxidizing ability. Ozone is a unique bacteriolysis preparation capable of quickly dissolving the cell wall, and destroying the internal structures of bacteria, viruses and other microorganisms, and therefore ozone has a strong killing effect on all kinds of pathogenic microorganisms. The sterilization process of ozone belongs to the biochemical oxidation reaction. Specifically, the sterilization function of the ozone is mainly achieved through the following ways:

(1) ozone can oxidize the enzymes for decomposing glucose in bacteria, inactivating and killing the bacteria; (2) ozone can act on nuclear substances in bacterial cells, such as purines and pyrimidines in nucleic acids, and destroy their organelles, DNA and RNA, so that the bacteria is killed by means of destroying the metabolism of the bacteria; (3) ozone participates in double chain reactions with cell wall lipids of the bacteria, invades the cell through the cell membrane and acts on lipoproteins of the outer membrane and lipopolysaccharides inside the cell membrane, which causes the bacteria to dissolve and die due to permeability transition; and (4) ozone acts on the four polypeptide chains of the capsid protein of the virus, damages RNA and destroys the proteins that form the virus.

The epidermis of the bacteriophage ozonized by ozone is broken into pieces, from which a lot of ribonucleic acid is released, and ozone prevents the ribonucleic acid from being attached to the host. However, in the process of the medical application of ozone, if users perform operations by mistake, the ozone is likely to be leaked, which will cause serious pollution to the environment, and even do harm to the users.

Therefore, it is desirable to provide an improved technical solution to solve the corresponding technical problems existing in the prior art.

SUMMARY

An objective of the present invention is to provide a series of structures to solve the technical problems existing in the prior art, which can well eliminate the problem of the ozone leakage caused by the use of ozone generated by the device, especially the use of gaseous ozone in the treatment process. The present invention provides a plurality of technical solutions to achieve the above objective.

Specifically, the present invention adopts the following technical solutions.

A sealing device for a foot therapeutic apparatus and a foot therapeutic apparatus with the sealing device are provided.

The sealing device for the foot therapeutic apparatus includes an airtight sleeve and a sealing member. The airtight sleeve includes a treatment box connecting end and a limb inlet end. The sealing member is fixedly mounted at the limb inlet end. The sealing member includes a tightening band and an annular gas bag located on the outer periphery of the tightening band. The annular gas bag is connected to a gas source.

The foot therapeutic apparatus includes a treatment chamber and an electrical chamber. The treatment chamber includes a treatment box, and the sealing device for the foot therapeutic apparatus is arranged on the treatment box. A box opening is arranged at the top of the treatment box, and the treatment box connecting end of the airtight sleeve of the sealing device is hermetically connected to the box opening.

The treatment box and the airtight sleeve constitute a treatment space, and the treatment space is used to place the patient's foot and/or leg with a lesion and form an ozone medical condition. In use, the patient's limb with a lesion passes through the limb inlet end into the treatment space for treatment, and the sealing member is configured to tightly seal the treatment space so that the ozone in the treatment space does not leak. The sealing member includes the tightening band and the annular gas bag located on the outer periphery of the tightening band. The tightening band is used to make the human limb and the airtight sleeve construct a primary sealing state at the limb inlet end, and then the annular gas bag expands gradually to supplement the pressure on the tightening band, so as to construct a secondary sealing state, thereby ensuring that the ozone cannot be leaked from the treatment space.

The whole treatment time is generally long and usually lasts a few minutes or dozens of minutes. During the treatment, the patient's limb will generate deformation (such as swelling, collapse) at the extrusion position. The tightening band is solely adopted, which cannot guarantee a high degree of sealing in the whole treatment process. Moreover, the excessively tight force applied to the patient's limb is very likely to lead to poor blood circulation for the patient's limb. As one of the necessary components of the sealing member, the annular gas bag is more elastic than the tightening band and has the flexibility of loosening and tightening the sealing member during the whole treatment process.

Preferably, an ozone discoloration reagent layer is arranged on the surface of the annular gas bag. More preferably, a wet-state potassium iodide aqueous solution layer is arranged on the surface of the annular gas bag. The leaked ozone can first be smelt by the user or other people nearby the device. However, this method is easily disturbed by other factors, especially the long-term trace leaked ozone is difficult to detect. By the ozone discoloration reagent layer provided on the surface of the annular gas bag, the people nearby the device such as patients can observe and determine the leaked ozone, which increases the reliability of identification. The potassium iodide aqueous solution is preferably selected as the ozone discoloration reagent. According to the chemical reaction: $O_3+2KI+H_2O=O_2+I_2+2KOH$, when elemental iodine is produced, the color change can be observed visually, and the varied scope of color or the degree of color contrast can reflect the amount of ozone participating in the reaction. Before treatment, the potassium iodide aqueous solution is coated on the surface of the annular gas bag to form a wet-state solution layer. In addition, according to the actual treatment time, the thickener is appropriately added to the potassium iodide aqueous solution to adjust the thickness of the layer and ensure the volatilization time.

Preferably, the sealing device for the foot therapeutic apparatus further includes a programmable logic controller (PLC) gas pressure regulating system. The PLC gas pressure regulating system includes a pressure sensor, a PLC, a relay and a solenoid valve. A signal output end of the pressure sensor is connected to a signal input end of the PLC, and a signal input end of the relay is connected to a signal output end of the PLC. A signal output end of the relay is connected to the solenoid valve, and the solenoid valve is connected to the gas source. The pressure sensor is a flexible pressure sensor and is arranged between the tightening band and the annular gas bag. The PLC gas pressure regulating system is used to adjust the gas pressure of the annular gas bag at the beginning of treatment or during the whole treatment process, so as to obtain appropriate internal pressure applied to the limb, construct and balance the relationship between the reasonable sealing and the bearing capacity of the limb. The flexible pressure sensor is located between the tightening band and the annular gas bag, and the flexible pressure sensor is mainly used to detect the mutual pressure relationship between the annular gas bag and the tightening band. The authenticity, change interval and reliability of the data obtained from the flexible pressure sensor arranged between the tightening band and the annular gas bag are greater than that of the flexible pressure sensor directly arranged between the limb and the tightening band, especially in the case that the excessively long treatment time leads to changes in the skin elasticity or appearance of the human limb or even serious deterioration.

In order to ensure the controllability of the gas stored in the annular gas bag, more preferably, a micro-breathable hole or a micro-breathable slit is arranged on the annular gas bag. The gas releases slightly and continuously to ensure that the gas pressure in the annular gas bag is always dynamically controllable, thus increasing the overall sealing reliability and comfort of the sealing member.

Preferably, the flexible pressure sensor includes a flexible substrate, and the material of the flexible substrate is selected from a metal material or a resin material. The metal material is selected from one or a composite laminated by least two of aluminum, aluminum alloy, copper, copper alloy, galvanized steel, nickel-based alloy, Inconel, titanium or titanium alloy. The resin material is selected from one or a composite laminated by at least two of ABS, polyformaldehyde (POM), butyl synthetic rubber, perfluorinated rubber, chlorinated polyvinyl chloride, ethylene propylene diene monomer (EPDM), tetrafluoroethylene, modified tetrafluoroethylene, alicyclic epoxy resin, ethylene-propylene, fluorosilicone rubber, fluorinated silicone rubber, low-density polyethylene (LDPE), polyvinylidene fluoride, polyacrylate, polycarbonate (PC), polysulfide, polyimide, polyurethane, polytetrafluoroethylene (PTFE), polyvinyl chloride (PVC), polyvinylidene fluoride (PVDF), vulcanized polypropylene/ethylene propylene diene monomer (PP/EPDM) rubber, silicone resin or polyethylene. Since the flexible pressure sensor possibly contacts or even continuously contacts the ozone, the material of the substrate must be inert relative to the ozone. If the material of the substrate is not inert to the ozone, then it is necessary to coat or process the surface of the substrate accordingly. Therefore, preferably, a sodium tetrafluoroethylene layer is coated on the surface of the flexible substrate. When the flexible substrate is made of aluminum or aluminum alloy, the surface of the flexible substrate is processed by micro-arc oxidation or low-temperature oxidation.

Preferably, the number of flexible pressure sensors is 2-4. Multiple flexible pressure sensors are arranged to reduce the requirement for each flexible pressure sensor, so that the conventional flexible pressure sensors can be applied in different situations. Furthermore, such redundancy can avoid the influence on the overall data acquisition when one or more of the flexible pressure sensors are not working properly on the signal acquisition or signal transmission. More preferably, the flexible pressure sensors are symmetrically arranged in the circumferential direction. In use, the pressure signal transmitted by the flexible pressure sensor can also be used to determine the specific skin condition of the sealing position of the human limb.

Preferably, a protrusion is arranged on a side of the tightening band facing the annular gas bag. The flexible pressure sensor includes a pressure sensitive layer region, and the protrusion is aligned with the pressure sensitive layer region. According to the technical solution of the present invention, the protrusion is configured to improve the contact tightness between the pressure sensitive layer of the flexible pressure sensor and the tightening band, which avoids the virtual connection because of the factors such as angle, tightness, surface structure shape of the human limb and others. In general, the thickness of the protrusion is small to ensure that there is no obvious deviation between the collected pressure value and the pressure value of other parts of the human limb, and the protrusion does not cause obvious discomfort or damage to the surface of the limb. More preferably, the protrusion is a solid structure, or a gas bag is arranged in the protrusion.

The present invention further provides a foot therapeutic apparatus, including a treatment chamber and an electrical chamber. The treatment chamber includes a treatment box, and the sealing device mentioned above for the foot therapeutic apparatus is arranged on the treatment box. A box opening is arranged at the top of the treatment box, and a treatment box connecting end of an airtight sleeve of the sealing device is hermetically connected to the box opening.

The treatment chamber is generally separated from the electrical chamber, but in some cases, the treatment chamber is integrally formed with the electrical chamber to form an integrated structure that can be identified in appearance. If a frame body is designed, the treatment chamber and the electrical chamber can be fixedly mounted on the frame body. When the foot therapeutic apparatus is a conventional fixing device, it can be designed to be fixed to a wall or a bed, or even be integrated with a bed, a table or a cabinet. When the foot therapeutic apparatus is designed as a movable device, wheels are usually fixed on the frame body.

Preferably, the treatment chamber further includes an outer housing, and the treatment box is located in the outer housing. The electrical chamber includes a mounting rack. An ozone generator and an ozone generation controller electrically connected to the ozone generator are fixedly connected on the mounting rack. The ozone generator communicates with the inside of the treatment box through a first gas path. The ozone generation principle of the ozone generator is various, for example, when using the ultraviolet irradiation method, the ozone generator usually includes an oxygen production device and an ultraviolet illumination device, and preferably, the oxygen production device usually adopts a molecular sieve.

Preferably, a medical solution atomization device is fixedly mounted on the mounting rack. The medical solution atomization device includes a storage tank, a control valve, a pump and an atomizer, which are successively connected. The control valve is further connected to a controller. In order to make the foot therapeutic apparatus provided by the present invention suitable for atomization treatment, in the technical solution of the present invention, a medical solution atomization device is fixedly mounted on the mounting rack. The atomized medical solution diffuses evenly in the treatment space and touches the lesion site of the patient in all directions, which is helpful to improve the treatment experience and feeling for the patient.

Preferably, an oxygen production device is fixedly mounted on the mounting rack. The oxygen production device includes a negative pressure fan, a compressor and a molecular sieve, which are successively connected. The molecular sieve communicates with the inside of the treatment box through a second gas path or the first gas path. The oxygen can not only be used for the preparation of ozone, but also play a corresponding role in the treatment of the lesion. The oxygen performs better in a high pressure condition, which is suitable for the sealing construction scheme provided by the present invention.

Preferably, a heating device is arranged between the outer housing and the treatment box. The heating device is configured to perform water bath heating, electrical heating or infrared heating. When the temperature in the treatment space is normal or relatively high, it is helpful for the ozone and the drugs to act on the foot lesion, and the rapid circulation rate of blood is promoted.

Preferably, the treatment box is entirely or partly made of transparent materials, and an ultraviolet sterilization device is fixedly mounted on the outside of a transparent part of the treatment box. Ultraviolet light can not only be used to prepare the ozone, but also disinfect the inside of the treatment box, which depends on the installation location and irradiation direction of the ultraviolet sterilization device. According to the above technical solution, due to the transparent part of the treatment box, the internal treatment space can be irradiated by the ultraviolet light. Hence, before and after the treatment, the cleanliness of the internal treatment space can be continuously ensured, so as to improve the treatment effect and the life of the apparatus.

Compared with the prior art, the advantage of the present invention is as follows.

The present invention can effectively prevent the leakage of ozone and improve the treatment experience of the patient.

Figure 1:
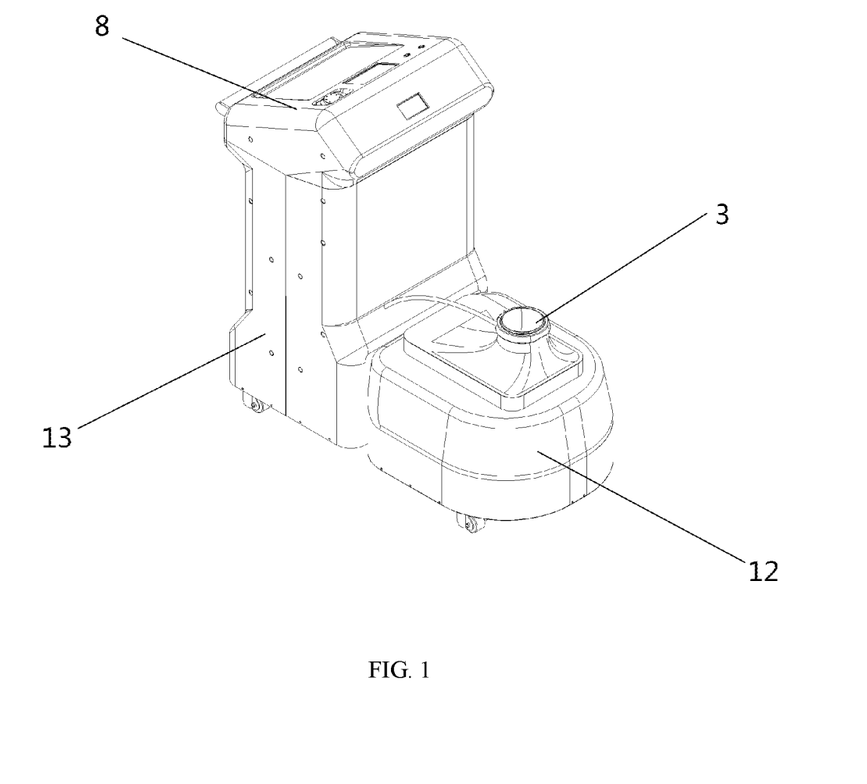
FIG. 1 is a first schematic diagram of the overall three-dimensional structure of the foot therapeutic apparatus.
Figure 2:
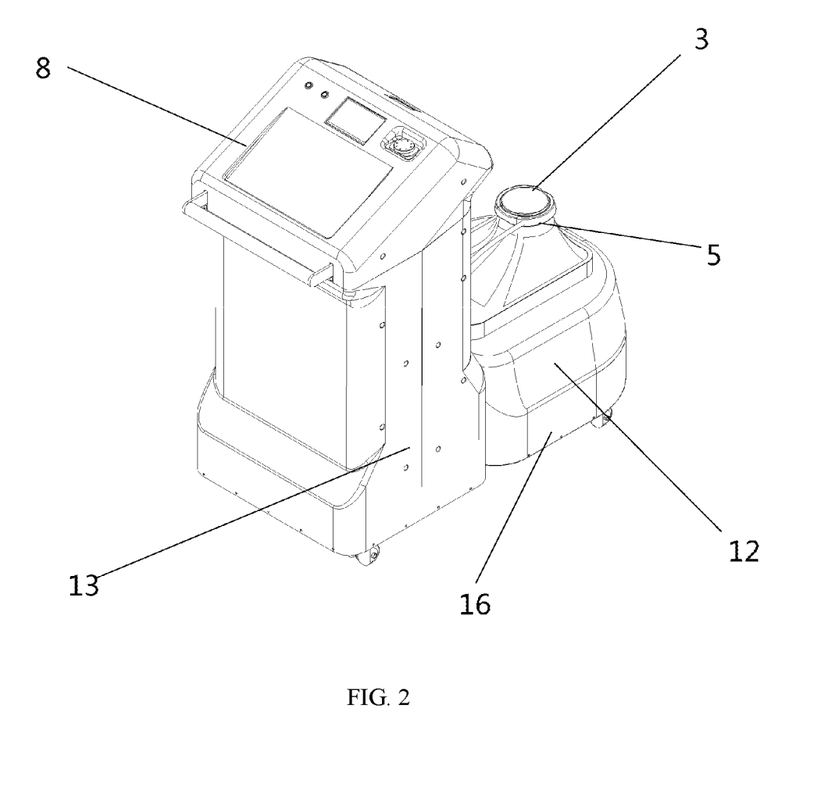
FIG. 2 is a second schematic diagram of the overall three-dimensional structure of the foot therapeutic apparatus.
Figure 3:
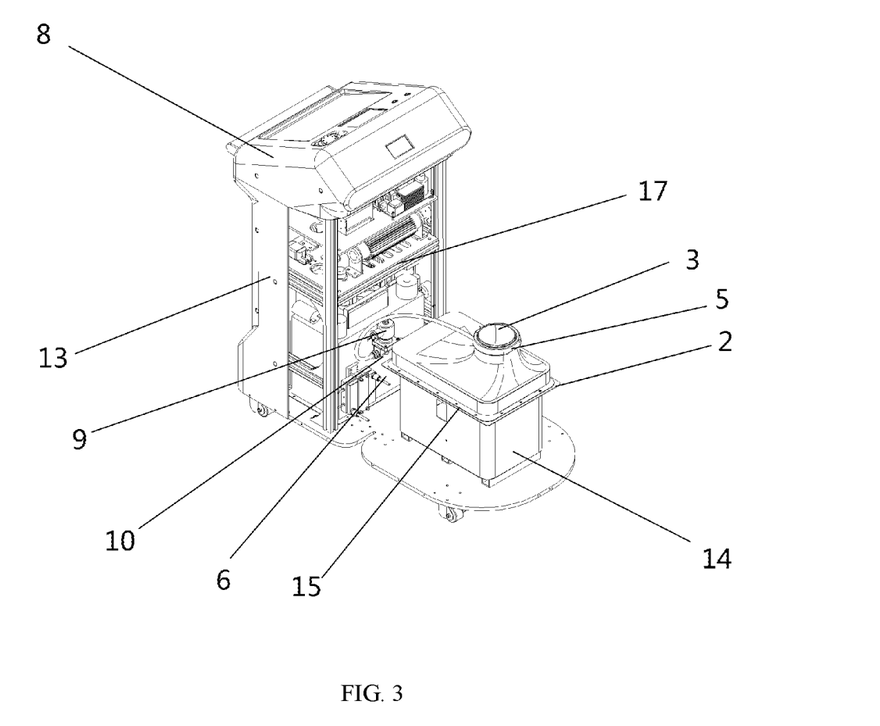
FIG. 3 is a schematic diagram of the partial three-dimensional structure of the foot therapeutic apparatus in FIG. 1 after removal of the housing.
Figure 4:
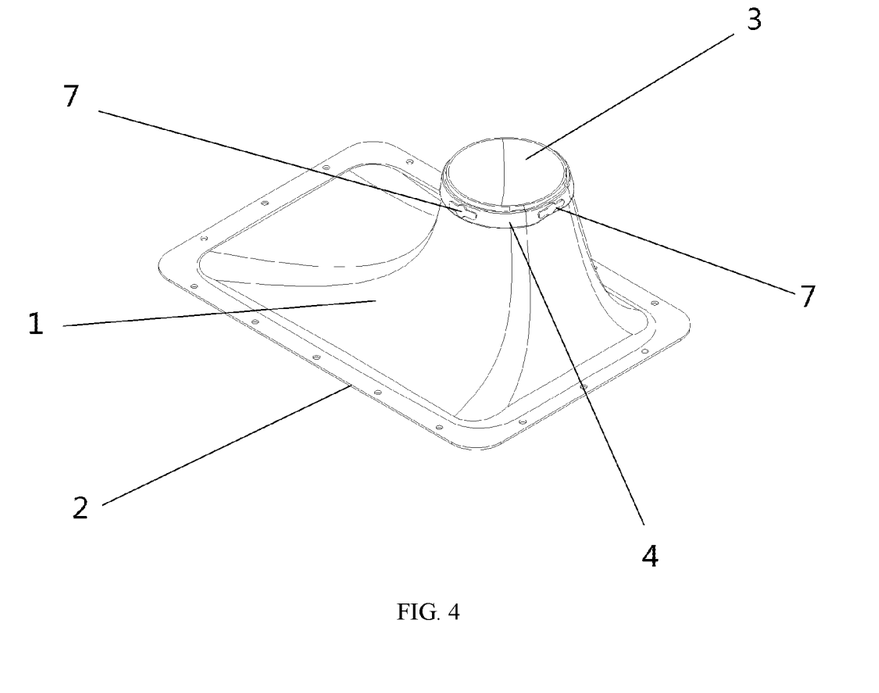
FIG. 4 is a first schematic diagram of the partial three-dimensional structure of the airtight sleeve of the foot therapeutic apparatus.
Figure 5:
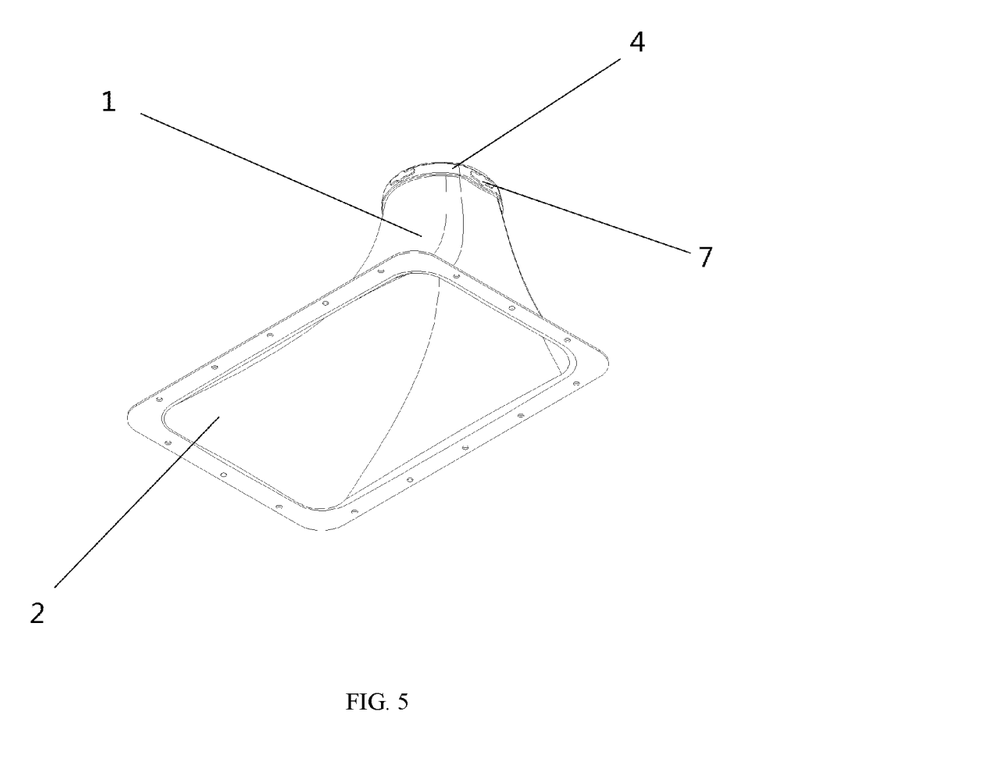
FIG. 5 is a second schematic diagram of the partial three-dimensional structure of the airtight sleeve of the foot therapeutic apparatus.
Figure 6:
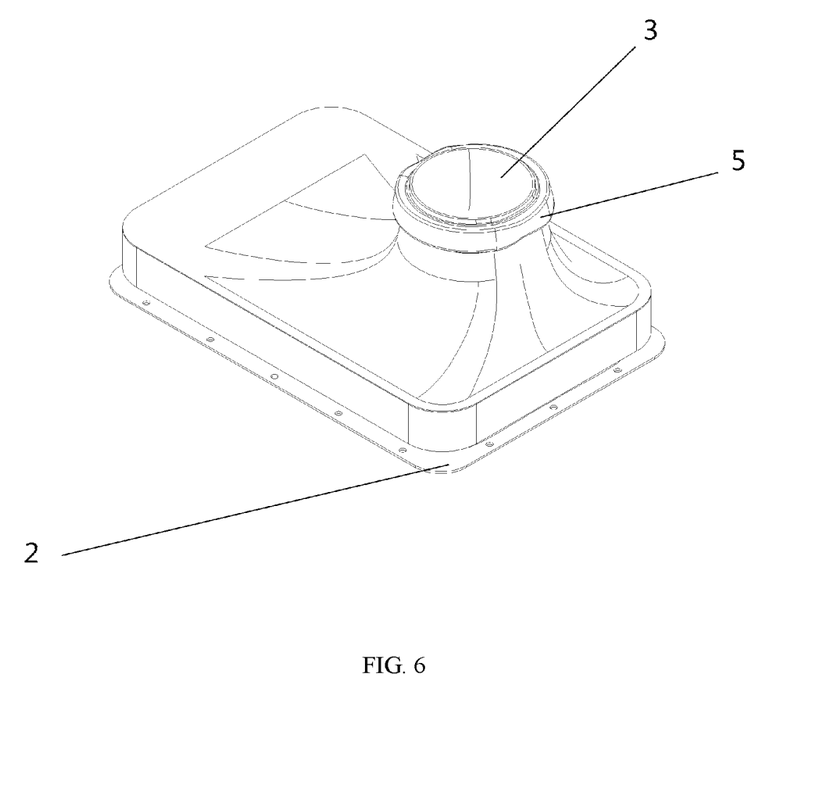
FIG. 6 is a first schematic diagram of the three-dimensional structure before inflation in case that the sealing member is completely mounted on the component in FIG. 4.
Figure 7:
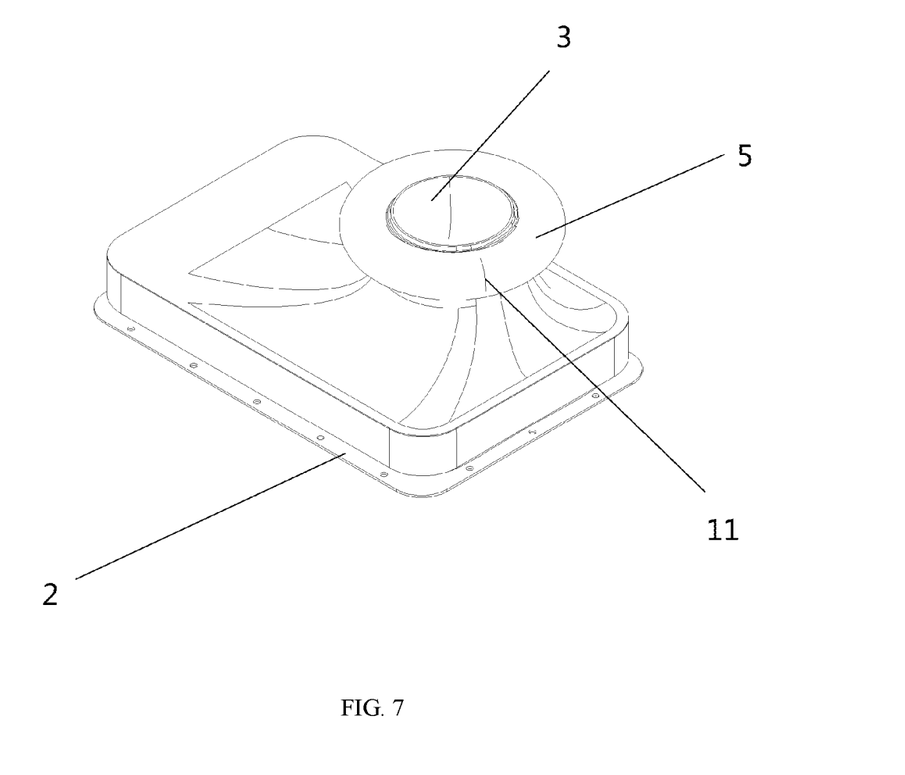
FIG. 7 is a second schematic diagram of the three-dimensional structure after inflation in case that the sealing member is completely mounted on the component in FIG. 4.
Figure 8:
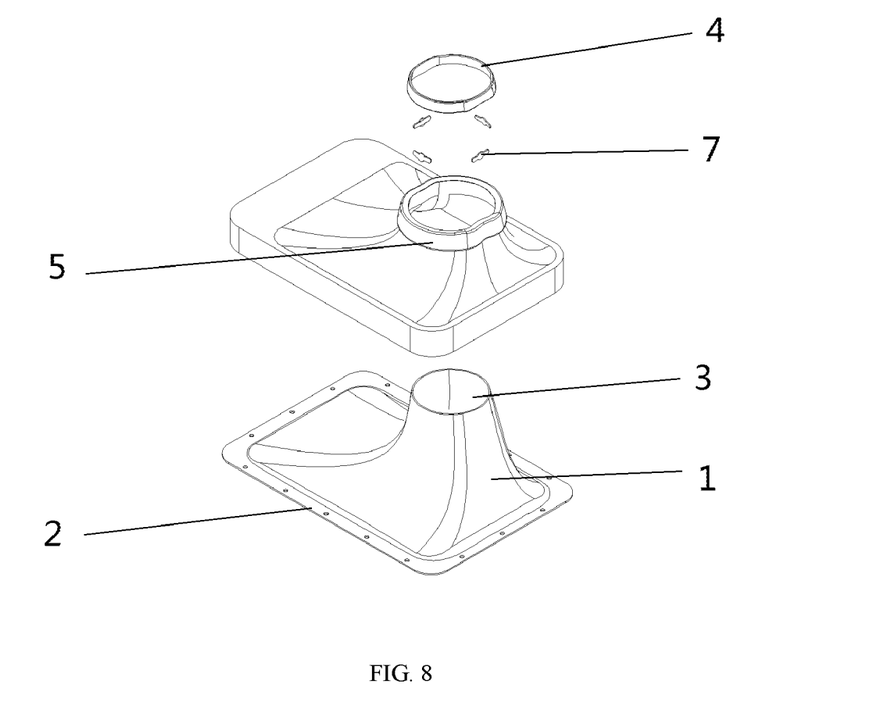
FIG. 8 is a first exploded view of the three-dimensional structure of the component in FIG. 6.
Figure 9:
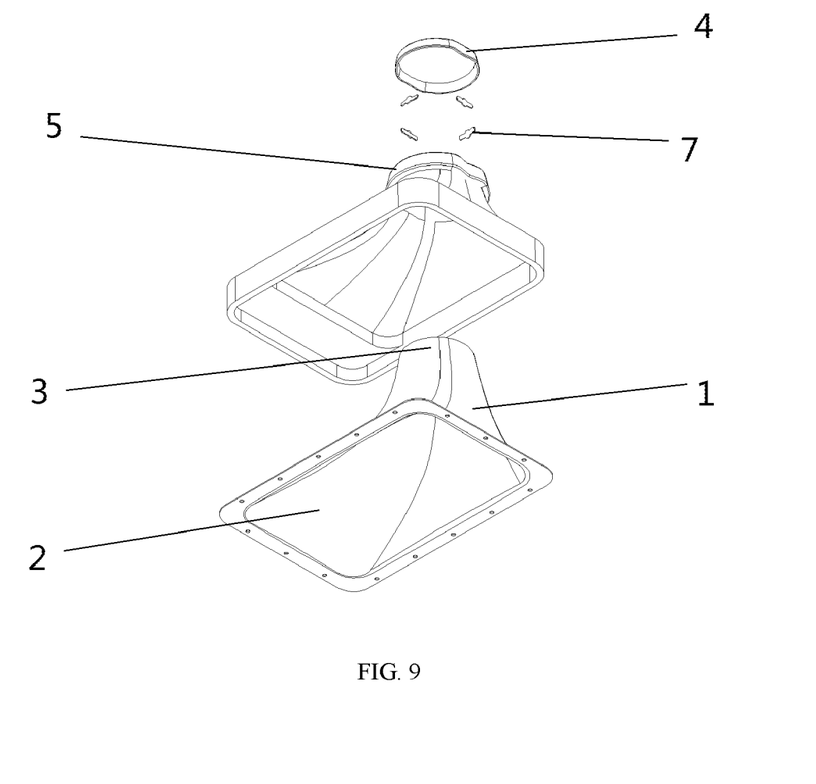
FIG. 9 is a second exploded view of the three-dimensional structure of the component in FIG. 6.

1. airtight sleeve, 2. treatment box connecting end, 3. limb inlet end, 4. tightening band, 5. annular gas bag, 6. gas source, 7. pressure sensor, 8. PLC, 9. relay, 10. solenoid valve, 11. micro-breathable slit, 12. treatment chamber, 13. electrical chamber, 14. treatment box, 15. box opening, 16. outer housing, 17. mounting rack.

DETAILED DESCRIPTION OF THE EMBODIMENTS

In one embodiment, a foot therapeutic apparatus includes treatment chamber 12 and the electrical chamber 13. The treatment chamber 12 is mounted in the outer housing 16. The treatment chamber 12 includes the treatment box 14, and a sealing device for the foot therapeutic apparatus is arranged on the treatment box 14. The box opening 15 is arranged at the top of the treatment box 14, and the treatment box connecting end 2 of the airtight sleeve 1 of the sealing device is hermetically in hot melt connection to the box opening 15. The electrical chamber 13 includes the mounting rack 17. An ozone generator, an ozone generation controller and other devices are mounted on the mounting rack 17.

The ozone generator communicates with the inside of the treatment box 14 through the first gas path, so that the generated ozone can enter into the treatment box 14. A unidirectional valve allowing the direction towards the treatment box 14 is mounted at the connection portion between the first gas path and the treatment box 14, so as to prevent the reverse flow of the ozone in a large range. The ozone generator includes a molecular sieve-type oxygen production device and an ultraviolet illumination device, and the gas can be further driven by a negative pressure gas pump or a fan.

In another embodiment, a medical solution atomization device is fixedly mounted on the mounting rack 17. The medical solution atomization device includes a storage tank, a control valve, a pump and an atomizer, which are successively connected. The control valve is further connected to a controller.

In another embodiment, an infrared heating device is mounted between the outer housing 16 and the treatment box 14. In the present embodiment, after the infrared heating device is turned on, the temperature is monitored and maintained constantly between 33° C. and 45° C. When the temperature reaches 45° C., the infrared heating device is turned off and cools naturally until reaching 33° C., thereby effectively preventing low-temperature thermal burn. The outer housing 16 is a three-layer structure, and includes a blackbody layer, an aluminum thermal conductive layer and a thermal insulation shell layer from the inside to the outside.

In another embodiment, the treatment box 14 is made entirely of transparent material, and an ultraviolet sterilization device is fixedly mounted on the outside of the treatment box 14.

The sealing device for the foot therapeutic apparatus includes the airtight sleeve 1 and a sealing member. The airtight sleeve 1 includes the treatment box connecting end 2 and the limb inlet end 3. The sealing member is fixedly mounted at the limb inlet end 3. The sealing member includes the tightening band 4 and the annular gas bag 5 located on the outer periphery of the tightening band 4. The annular gas bag 5 is connected to the gas source 6. The tightening band 4 is a magic tape. The gas source 6 is a gas pump or a high-pressure gas cylinder, and a replaceable high-pressure gas cylinder is selected in the present embodiment. A wet-state potassium iodide aqueous solution layer is coated on the surface of the annular gas bag 5. The potassium iodide aqueous solution is used to visually monitor the leak of the ozone. Four flexible pressure sensors are arranged between the tightening band 4 and the annular gas bag 5. In the present embodiment, the SI4-G soft ultra-thin pressure sensors of China Hanwei Technology Group Co., Ltd. are selected and arranged symmetrically around the circumference of the human limb. In the present embodiment, the four pressure sensors 7 are fixed on the inner surface of the annular gas bag 5 in advance. Of course, the pressure sensors 7 can also be added later or fixed on the tightening band 4 in advance. The signal output end of the flexible pressure sensor is connected to the signal input end of the programmable logic controller (PLC) 8. Alternatively, a digital-analog converter module for the digital-analog conversion is further provided according to different devices. The signal input end of the relay 9 is connected to the signal output end of the PLC 8, the signal output end of the relay 9 is connected to the solenoid valve 10, and the solenoid valve 10 is connected to the high-pressure gas cylinder. According to the predetermined scope of the gas pressure, the solenoid valve 10 is turned off to maintain the internal gas pressure of the annular gas bag 5 at a constant interval value, and the solenoid valve 10 is turned on to activate the high-pressure gas cylinder to inflate the annular gas bag 5, which can ensure the sealing degree, and adjust the relationship between the sealing reliability and the comfort degree.

In another embodiment, the micro-breathable slit 11 is arranged on the annular gas bag 5, and the micro-breathable slit 11 is configured to dynamically adjust the pressure range of the annular gas bag 5 by deflating slowly, thereby preventing the annular gas bag 5 from maintaining at a high-pressure range all the time.

Four miniature rigid protrusions with a thickness of 0.15 cm are arranged on the outer surface of the tightening band 4, and each miniature rigid protrusion corresponds to the pressure sensitive layer region of the flexible pressure sensor at the corresponding position. Alternatively, the protrusion has a soft structure with a gas bag inside.

In the present embodiment, the polytetrafluoroethylene, a pure aluminum multilayer film with micro-arc oxidation and the acrylonitrile butadiene styrene (ABS) coated with a sodium tetrafluoroethylene film are separately selected as a substrate material.

In addition, the selected substrate material is required to be inert relative to the ozone, so in some embodiments, the substrate material may also be a metal material or a resin material. The metal material can be selected from one or a composite laminated by least two of aluminum, aluminum alloy, copper, copper alloy, galvanized steel, nickel-based alloy, Inconel, titanium or titanium alloy. The resin material can be selected from one or a composite laminated by at least two of ABS, polyformaldehyde (POM), butyl synthetic rubber, perfluorinated rubber, chlorinated polyvinyl chloride, ethylene propylene diene monomer (EPDM), tetrafluoroethylene, modified tetrafluoroethylene, alicyclic epoxy resin, ethylene-propylene, fluorosilicone rubber, fluorinated silicone rubber, low-density polyethylene (LDPE), polyvinylidene fluoride, polyacrylate, polycarbonate (PC), polysulfide, polyimide, polyurethane, polytetrafluoroethylene (PTFE), polyvinyl chloride (PVC), polyvinylidene fluoride (PVDF), vulcanized polypropylene/ethylene propylene diene monomer (PP/EPDM) rubber, silicone resin or polyethylene.

What is claimed is:

1. A sealing device for a foot therapeutic apparatus, comprising:
    an airtight sleeve, wherein, the airtight sleeve comprises a treatment box connecting end and a limb inlet end; and
    a sealing member fixedly mounted at the limb inlet end, wherein, the sealing member comprises a tightening band and an annular gas bag located on an outer periphery of the tightening band; the annular gas bag is connected to a gas source.

2. The sealing device of claim 1, wherein, an ozone discoloration reagent layer is arranged on a surface of the annular gas bag.

3. The sealing device of claim 2, wherein, a wet-state potassium iodide aqueous solution layer is arranged on the surface of the annular gas bag.

4. The sealing device of claim 1, further comprising a programmable logic controller (PLC) gas pressure regulating system; wherein the PLC gas pressure regulating system comprises a pressure sensor, a PLC, a relay and a solenoid valve; a signal output end of the pressure sensor is connected to a signal input end of the PLC, and a signal input end of the relay is connected to a signal output end of the PLC; a signal output end of the relay is connected to the solenoid valve, and the solenoid valve is connected to the gas source; and the pressure sensor is a flexible pressure sensor and is arranged between the tightening band and the annular gas bag.

5. The sealing device of claim 4, wherein, a micro-breathable hole or a micro-breathable slit is arranged on the annular gas bag.

6. The sealing device for the foot therapeutic apparatus of claim 5, wherein, the flexible pressure sensor comprises a flexible substrate, and a material of the flexible substrate is selected from a metal material or a resin material; wherein, the metal material is one selected from a first group consisting of aluminum, aluminum alloy, copper, copper alloy, galvanized steel, nickel-based alloy, Inconel, titanium or titanium alloy; or, the metal material is a composite laminated by least two selected from the first group; and the resin material is one selected from a second group consisting of acrylonitrile butadiene styrene (ABS), polyformaldehyde (POM), butyl synthetic rubber, perfluorinated rubber, chlorinated polyvinyl chloride, ethylene propylene diene monomer (EPDM), tetrafluoroethylene, modified tetrafluoroethylene, alicyclic epoxy resin, ethylene-propylene, fluorosilicone rubber, fluorinated silicone rubber, low-density polyethylene (LDPE), polyvinylidene fluoride, polyacrylate, polycarbonate (PC), polysulfide, polyimide, polyurethane, polytetrafluoroethylene (PTFE), polyvinyl chloride (PVC), polyvinylidene fluoride (PVDF), vulcanized polypropylene/ethylene propylene diene monomer (PP/EPDM) rubber, silicone resin or polyethylene; or, the resin material is a composite laminated by at least two selected from the second group.

7. The sealing device of claim 5, wherein, a number of flexible pressure sensors is 2-4.

8. The sealing device for the foot therapeutic apparatus of claim 4, wherein, the flexible pressure sensor comprises a flexible substrate, and a material of the flexible substrate is selected from a metal material or a resin material; wherein, the metal material is one selected from a first group consisting of aluminum, aluminum alloy, copper, copper alloy, galvanized steel, nickel-based alloy, Inconel, titanium or titanium alloy; or, the metal material is a composite laminated by least two selected from the first group; and the resin material is one selected from a second group consisting of acrylonitrile butadiene styrene (ABS), polyformaldehyde (POM), butyl synthetic rubber, perfluorinated rubber, chlorinated polyvinyl chloride, ethylene propylene diene monomer (EPDM), tetrafluoroethylene, modified tetrafluoroethylene, alicyclic epoxy resin, ethylene-propylene, fluorosilicone rubber, fluorinated silicone rubber, low-density polyethylene (LDPE), polyvinylidene fluoride, polyacrylate, polycarbonate (PC), polysulfide, polyimide, polyurethane, polytetrafluoroethylene (PTFE), polyvinyl chloride (PVC), polyvinylidene fluoride (PVDF), vulcanized polypropylene/ethylene propylene diene monomer (PP/EPDM) rubber, silicone resin or polyethylene; or, the resin material is a composite laminated by at least two selected from the second group.

9. The sealing device of claim 8, wherein, a sodium tetrafluoroethylene layer is coated on a surface of the flexible substrate.

10. The sealing device of claim 8, wherein, when the flexible substrate is made of aluminum or aluminum alloy, a surface of the flexible substrate is processed by micro-arc oxidation or low-temperature oxidation.

11. The sealing device of claim 4, wherein, a number of flexible pressure sensors is 2-4.

12. The sealing device of claim 11, wherein, the flexible pressure sensors are symmetrically arranged on a circumference.

13. The sealing device of claim 4, wherein, a protrusion is arranged on a side of the tightening band, and the side of the tightening band faces the annular gas bag; the flexible pressure sensor comprises a pressure sensitive layer region, and the protrusion is aligned with the pressure sensitive layer region.

14. The sealing device of claim 13, wherein, the protrusion is a solid structure, or a gas bag is arranged in the protrusion.

15. A foot therapeutic apparatus, comprising a treatment chamber and an electrical chamber; wherein, the treatment chamber comprises a treatment box, and the sealing device of claim 1 is arranged on the treatment box; a box opening is arranged at a top of the treatment box, and the treatment box connecting end of the airtight sleeve of the sealing device is hermetically connected to the box opening.

16. The foot therapeutic apparatus of claim 15, wherein, the treatment chamber further comprises an outer housing, and the treatment box is located in the outer housing; the electrical chamber comprises a mounting rack; an ozone generator and an ozone generation controller electrically connected to the ozone generator are fixedly connected on the mounting rack; the ozone generator communicates with an inside of the treatment box through a first gas path.

17. The foot therapeutic apparatus of claim 16, wherein, a medical solution atomization device is fixedly mounted on the mounting rack; the medical solution atomization device comprises a storage tank, a control valve, a pump and an atomizer, and the storage tank, the control valve, the pump and the atomizer are successively connected; the control valve is connected to a controller.

18. The foot therapeutic apparatus of claim 16, wherein, an oxygen production device is fixedly mounted on the mounting rack; the oxygen production device comprises a negative pressure fan, a compressor and a molecular sieve, and the negative pressure fan, the compressor and the molecular sieve are successively connected; the molecular sieve communicates with the inside of the treatment box through a second gas path or the first gas path.

19. The foot therapeutic apparatus of claim 16, wherein, a heating device is arranged between the outer housing and the treatment box.

20. The foot therapeutic apparatus of claim 16, wherein, the treatment box is entirely or partly made of transparent material, and an ultraviolet sterilization device is fixedly mounted on an outside of a transparent part of the treatment box.

* * * * *